US010716601B2

(12) United States Patent
Schafer et al.

(10) Patent No.: US 10,716,601 B2
(45) Date of Patent: *Jul. 21, 2020

(54) SPINAL ALIGNMENT FRAME

(71) Applicant: NuVasive, Inc., San Diego, CA (US)

(72) Inventors: Andrew Schafer, Ramona, CA (US);
Robert German, San Diego, CA (US);
Jim A Youssef, Durango, CO (US);
Scott Lish, Oceanside, CA (US); Justin Doose, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/051,482

(22) Filed: Jul. 31, 2018

(65) Prior Publication Data
US 2019/0021772 A1    Jan. 24, 2019

Related U.S. Application Data

(63) Continuation of application No. 15/295,783, filed on Oct. 17, 2016, now Pat. No. 10,034,695, which is a continuation of application No. 14/214,099, filed on Mar. 14, 2014, now Pat. No. 9,480,504.

(60) Provisional application No. 61/794,723, filed on Mar. 15, 2013.

(51) Int. Cl.
*A61B 17/70* (2006.01)
*A61B 17/68* (2006.01)

(52) U.S. Cl.
CPC ........ *A61B 17/7079* (2013.01); *A61B 17/708* (2013.01); *A61B 17/7035* (2013.01); *A61B 17/7077* (2013.01); *A61B 17/7083* (2013.01); *A61B 2017/681* (2013.01)

(58) Field of Classification Search
CPC ............ A61F 2/4657; A61F 2002/4668; A61F 2002/30617; A61B 17/7076; A61B 17/7083
See application file for complete search history.

(56) References Cited

U.S. PATENT DOCUMENTS

| | | | |
|---|---|---|---|
| 5,201,734 A | 4/1993 | Cozad et al. |
| 7,597,694 B2 | 10/2009 | Lim et al. |
| 7,611,522 B2 | 11/2009 | Gorek |
| 7,914,536 B2 | 3/2011 | MacDonald et al. |
| 7,922,731 B2 | 4/2011 | Schumacher et al. |
| 7,947,046 B2 | 5/2011 | Justis et al. |
| 7,981,115 B2 | 7/2011 | Justis et al. |
| 7,998,144 B2 | 8/2011 | Schumacher et al. |
| 8,657,825 B2 | 2/2014 | Justis et al. |

(Continued)

FOREIGN PATENT DOCUMENTS

| | | |
|---|---|---|
| CN | 200987699 | 12/2007 |
| CN | 201337505 | 11/2009 |

(Continued)

*Primary Examiner* — Ellen C Hammond
*Assistant Examiner* — Tara Rose E Carter

(57) ABSTRACT

Disclosed is a surgical alignment and distraction frame and associated methods of use that facilitates correction of a sagittal imbalance. The alignment and distraction frame works in conjunction with pedicle screw installation guide assemblies to impart the desired correction. The alignment frame can be utilized to ensure the pedicle screw housings are aligned (to facilitate rod coupling) in concert with the completion of a correction maneuver.

20 Claims, 9 Drawing Sheets

(56) References Cited

U.S. PATENT DOCUMENTS

| | | |
|---|---|---|
| 8,702,713 B2 | 4/2014 | Nayet et al. |
| 8,911,442 B2 | 12/2014 | Wing et al. |
| 9,211,149 B2 | 12/2015 | Hoefer et al. |
| 9,402,660 B2 | 8/2016 | Brinkman et al. |
| 2005/0080418 A1* | 4/2005 | Simonson ............ A61B 17/025 606/86 A |
| 2006/0085010 A1 | 4/2006 | Lieberman |
| 2008/0077155 A1 | 3/2008 | Diederich et al. |
| 2008/0147079 A1 | 6/2008 | Chin et al. |
| 2009/0076515 A1 | 3/2009 | Lamartina et al. |
| 2010/0030283 A1* | 2/2010 | King .................. A61B 17/7037 606/86 A |
| 2010/0082066 A1 | 4/2010 | Biyani |
| 2010/0087823 A1 | 4/2010 | Kondrashov |
| 2010/0274252 A1 | 10/2010 | Bottomley et al. |
| 2012/0071885 A1 | 3/2012 | Forton et al. |
| 2013/0184763 A1 | 7/2013 | McClintock et al. |
| 2013/0245692 A1 | 9/2013 | Hayes et al. |
| 2013/0289633 A1 | 10/2013 | Gleeson et al. |
| 2014/0107659 A1* | 4/2014 | Walters .............. A61B 17/7074 606/102 |
| 2015/0066088 A1 | 3/2015 | Brinkman et al. |
| 2017/0079689 A1 | 3/2017 | Prevost |

FOREIGN PATENT DOCUMENTS

| | | |
|---|---|---|
| CN | 201642304 | 11/2010 |
| CN | 202699270 | 1/2013 |
| CN | 202723973 | 2/2013 |
| EP | 0528177 | 2/1993 |
| JP | 4810698 | 2/1993 |

\* cited by examiner

SPINAL ALIGNMENT FRAME

CROSS REFERENCES TO RELATED APPLICATIONS

The present application is a Continuation of U.S. application Ser. No. 14/214,099, filed Mar. 14, 2014, (currently pending). U.S. application Ser. No. 14/214,099 is a non-provisional application claiming the benefit of priority under 35 U.S.C. § 119(e) from commonly owned and U.S. Provisional Application Ser. No. 61/794,723 filed on Mar. 15, 2013 and entitled "Spinal Alignment Frame," the entire contents of which is hereby incorporated by reference into this disclosure as if set forth fully herein.

FIELD

The present application relates to the field of spinal surgery and spinal fixation devices, including a system and associated methods for manipulating, distracting and/or reorienting vertebrae of the spine in conjunction with the installation of a spinal fixation construct.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. Disruptions can be caused by any number factors including normal degeneration that comes with age, trauma, or various medical conditions. If a disruption to the spine becomes severe enough, damage to a nerve or part of the spinal cord may occur and can result in partial to total loss of bodily functions (e.g., walking, talking, breathing, etc.). Therefore, it is of great interest and concern to be able to treat and correct ailments of the spine.

When conservative efforts fail, treating spinal ailments very often includes one of or a combination of spinal fusion and fixation. Generally, spinal fusion procedures involve removing some or all of an intervertebral disc, and inserting one or more intervertebral implants into the resulting disc space. Introducing the intervertebral implant serves to restore the height between adjacent vertebrae ("disc height") and maintain the height, and/or correct vertebral alignment issues, until bone growth across the disc space connects the adjacent vertebral bodies. Resection of ligaments and/or honey elements from the affected spinal area is also common in order to access the disc space and/or decompress impinged nerve or spinal cord tissue.

Fixation systems are often surgically implanted during a fusion procedure to help stabilize the vertebrae to be fused until the fusion is complete or to address instabilities (either preexisting or created by the fusion or decompression procedure itself). Fixation constructs of various forms are well known in the art. Most commonly, the fixation construct is a plate anchored to the anterior column with multiple bone anchors or a posterior fixation construct including multiple anchors and a connecting rod anchored to the posterior elements of the spine. For a posterior fixation construct the anchors (typically pedicle screws) are anchored into the pedicles of each vertebra of the target motion segment. The pedicle is a dense, strong, stem-like structure that projects from the posterior side of the vertebral body. The anchors are then connected by a fixation rod that is locked to each anchor, thus eliminating motion between the adjacent vertebrae of the motion segment. The fixation anchors utilized in posterior fixation constructs generally include an anchor shank and a rod housing. The rod housing includes a pair of upstanding arms separated by a rod channel in which the fixation rod is captured and locked. When constructing the posterior fixation construct the surgeon must align and seat the rod in the rod channel. This can be a challenge as it requires the rod channels of adjacent rod housings to be generally aligned, or alternatively, the rod must be bent to fit.

In addition to simply stabilizing the spine, components of the fixation system can also be utilized to manipulate the positioning of the vertebrae to achieve the desired alignment before movement is arrested. That is, applying a directional force to the anchor shank through the attached housing, for example, via minimally invasive guides, reduction tools, or other instruments that are commonly engaged to the housing and extend out of the patient, causes the associated vertebra to translate or rotate in the direction of the force, thus allowing the surgeon good control to manipulate the relevant vertebrae into a desired position. However, doing so typically causes the rod housings to move relative to each other. Thus, achieving the desired correction (realignment) of the vertebrae while also aligning the rod channels of the housings to effectively seat a rod is a significant challenge and can create difficulties and delays during the surgery.

BRIEF DESCRIPTION OF THE DRAWINGS

FIG. 4D is an exploded view of the indicating and readout arm and related frame structure of FIG. 4A;

DETAILED DESCRIPTION

Various embodiments disclosed herein include surgical measurement frames that can be conveniently used by a surgeon to determine an appropriate surgical correction for a patient suffering from a spinal instability or deformity. For example, the surgical measurement frame may be used to realign sagittal balance during compression fracture reduction, VBR resection, pedicle subtraction osteotomy (PSO), scoliosis correction, or other procedures affecting sagittal balance.

Figure 1:
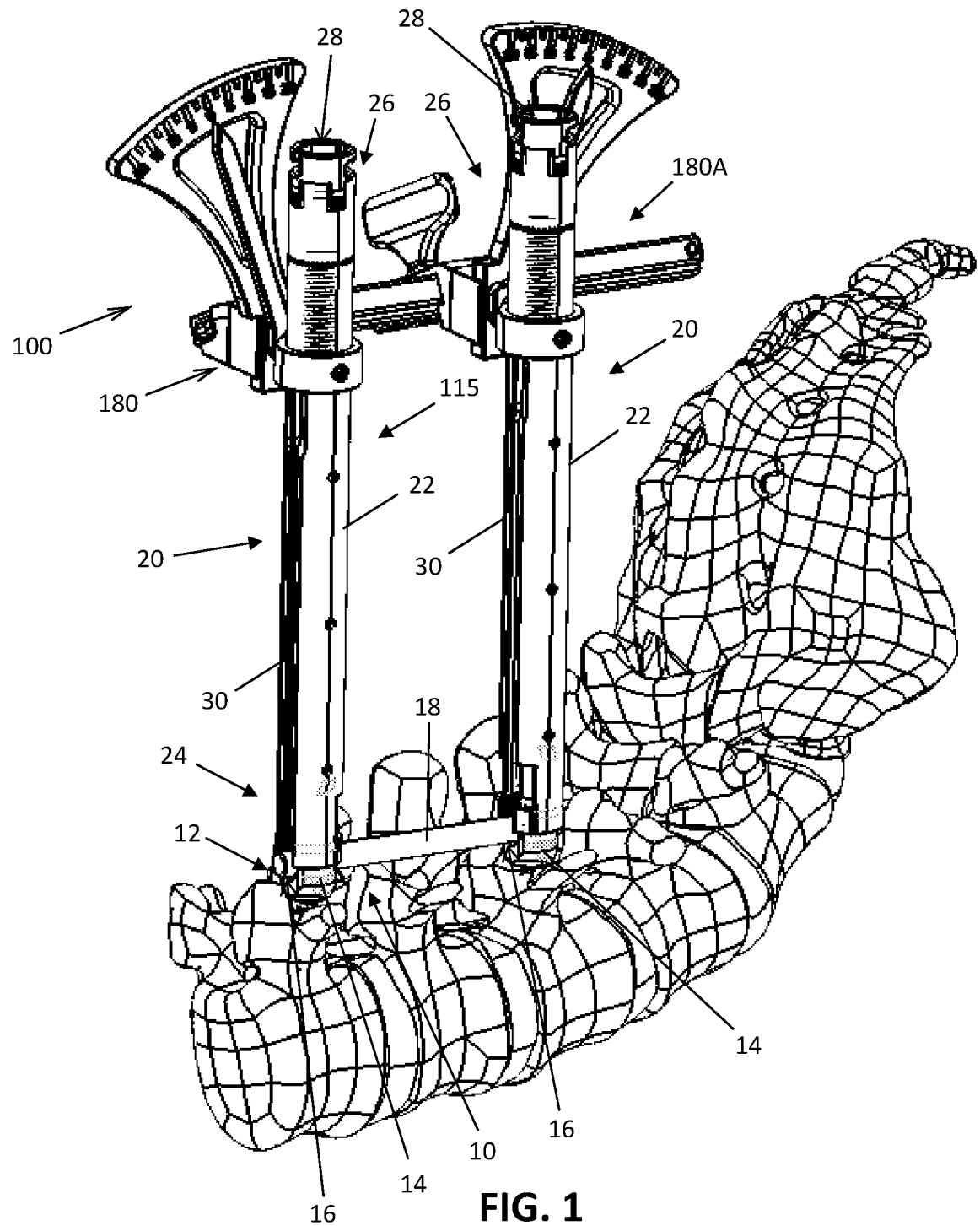
FIG. 1 is a perspective view of a spinal fixation system applied to a lumbar spine and having coupled thereto one example embodiment of a spinal alignment frame for facilitating manipulation of spinal anatomy to correct spinal imbalances.

With reference to FIG. 1, there is shown a spinal fixation construct 10 and associated installation guide assemblies 20, coupled with an example embodiment of a spinal alignment frame 100. The spinal fixation construct is of a type commonly known in the art and includes a pair of pedicle screws 12 and a rod 18. The pedicle screws 12 each include a rod housing 14 and a shank (not pictured) coupled to the housing. The housing 14 has pair of upstanding arms separated by a rod channel 16 in which the fixation rod 18 is captured and locked with a locking cap (not shown). The housing 14 is coupled to the shank in a manner that permits polyaxial rotation of the housing 14 relative to the shank. Locking of the rod 18 within the housing 14 also locks the housing 14, arresting further movement between the housing and the shank. Additionally, the pedicle screw 12 includes a provisional locking feature, various different embodiments of which are readily known and available in the art, which permits the housing 14 to be locked (again, arresting further movement between the housing 14 and the shank) before locking (or positioning) the rod 18. The provisional locking feature may be either reversible or irreversible.

The installation guide assemblies 20 are also of a type commonly known in the art and includes a generally tubular body 22 with a distal end 24 that releasably couples to the rod housing 14 and a proximal end 26 that extends out of the patient when the pedicle screw 12 is anchored to the vertebra and the distal end 22 is coupled to the housing 14. A lumen 28 extends through the body 22, opening in each of the distal end 24 and proximal end 26. Guide channels 30 passing through the body 20 and opening in the distal end 24, and preferably extending along a length of the guide toward the proximal end 26, align with the rod channel 16 when the guide and screw are coupled. The installation guides 20 facilitate rod delivery into the rod channels 16 and also facilitate engagement of various instruments with the pedicle screw. For example, a shank driver may extend through the lumen 28 to engage the shank, which also functions as a pseudo provisional lock, as the guide 20 (and thus the housing 14) is restrained from movement relative to the shank by the driver. Other instruments, such as a provisional locking tool used to engage (or disengage) the provisional lock, locking caps, and reducers may also be advanced through the lumen 28 to engage the screw 12. Additionally, the guide assemblies 20 can be manipulated from outside the body to impart force on the shank, via housing 14 (with the housing 14 locked), to adjust the position of the associated vertebra and achieve a desired surgical correction. By way of example, the guides may be manipulated to compress, distract, translate, rotate, and/or bend the associated vertebra relative to other vertebrae. It will be appreciated that while installation guides are generally used to facilitate minimally invasive pedicle fixation, the guides 20 (and the alignment frame 100 with them) may be utilized in open pedicle fixation procedures as well.

Figure 2:
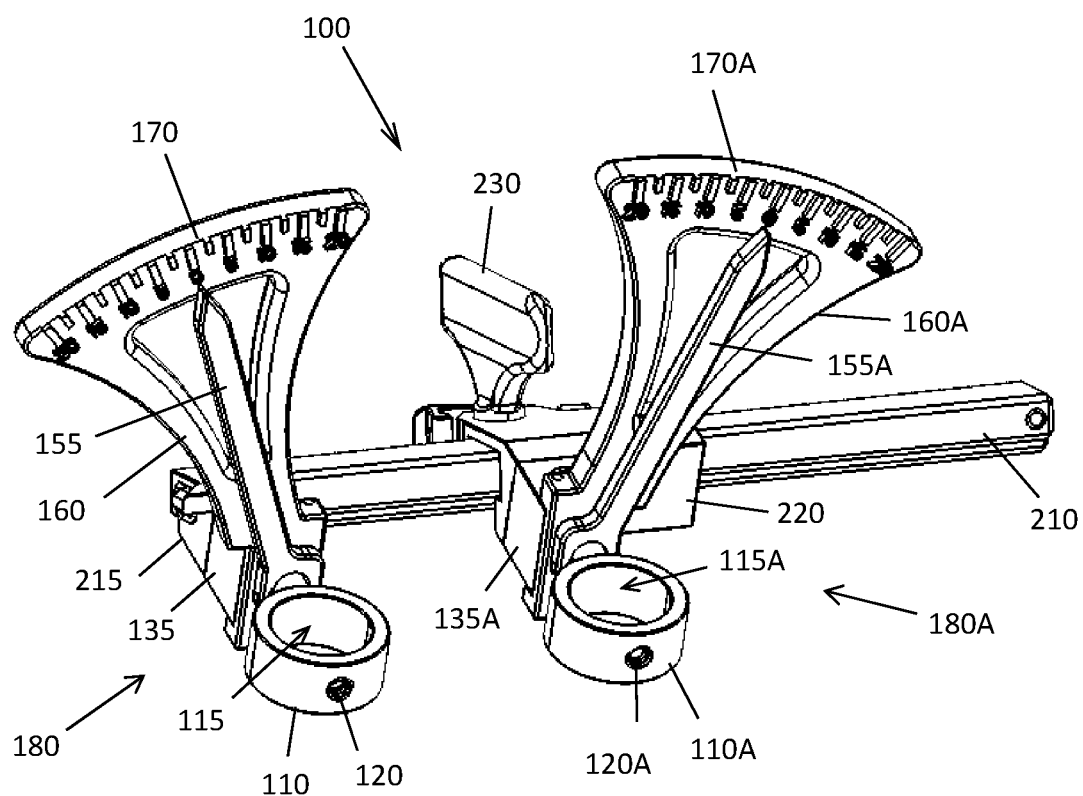
FIG. 2 is a perspective view of the alignment frame of FIG. 1.

FIG. 2 depicts the spinal alignment and distraction frame 100. The frame 100 includes a pair of guide attachment rings 110 and 110A, each of which has an internal opening 115 and 115A sized to fit over a single guide 20, such as those depicted in FIG. 1. Each of the guide attachment rings 110 and 110A include anterior openings 120 and 120A for accommodating a set screw (not shown) or other securement feature that allows the ring to be "locked" or otherwise secured to a desired position on the tubular guide 20. In various embodiments the guide 20 may include one or more grooves, notches, depressions or openings on an outer surface that accommodates the set screw (or clip, lever, etc.), allowing the ring 110 and 110A to be secured to a predetermined longitudinal and/or rotational position on the guide 20, or alternatively, the set screw may directly engage the outer surface of the guide body 22. In various alternative embodiments, attachment mechanisms other than rings could be utilized to attach the frame to the tubular guides, which could include locking tabs, screw and thread mechanisms, quick release tabs, slide locks, collets, inserts, taper and press fits or other connecting arrangements known in the art. For example, one alternative attachment mechanism includes attachment via a cap that clips onto the top of the tubular guides, or that could engage a projection, slot, ring or other feature on or extending outward of the guides.

Figure 3A:
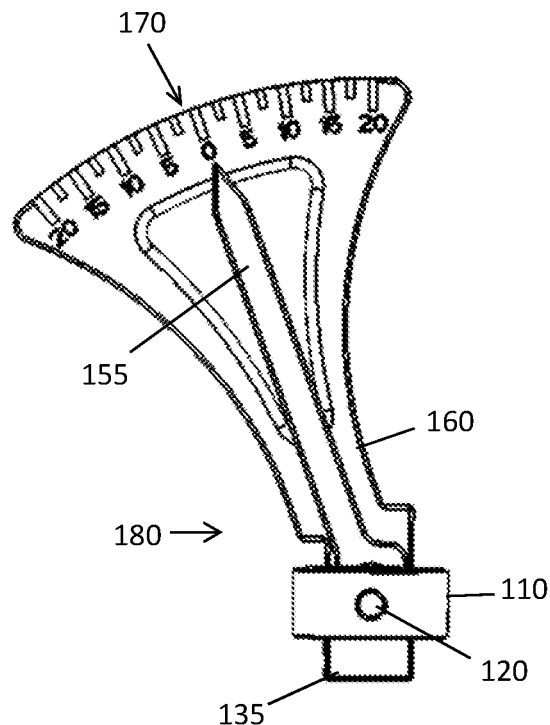
FIGS. 3A through 3C depict various perspective views of a left-side indicating and readout arm of the spinal alignment frame of FIG. 1.
Figure 3B:
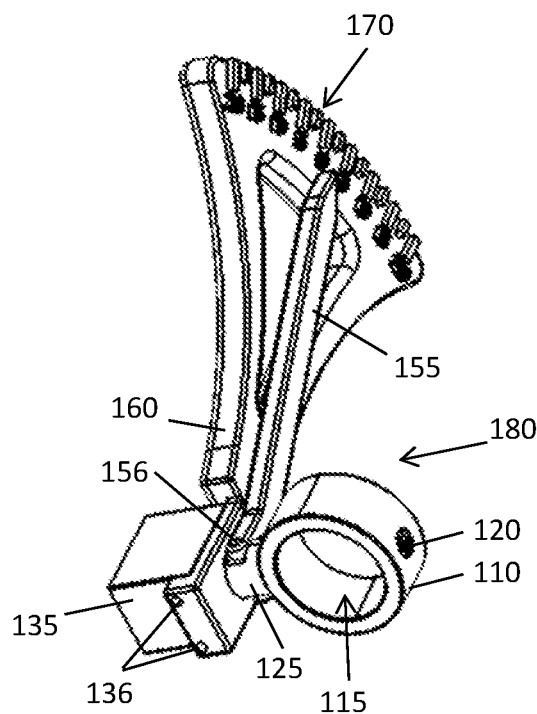
Figure 3C:
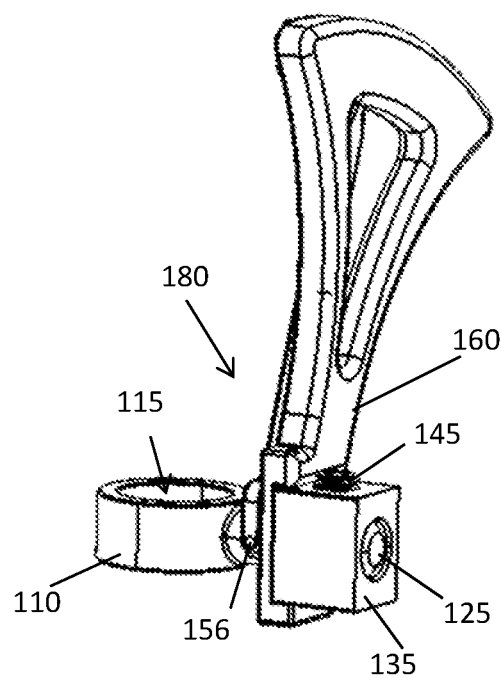
Figure 3D:
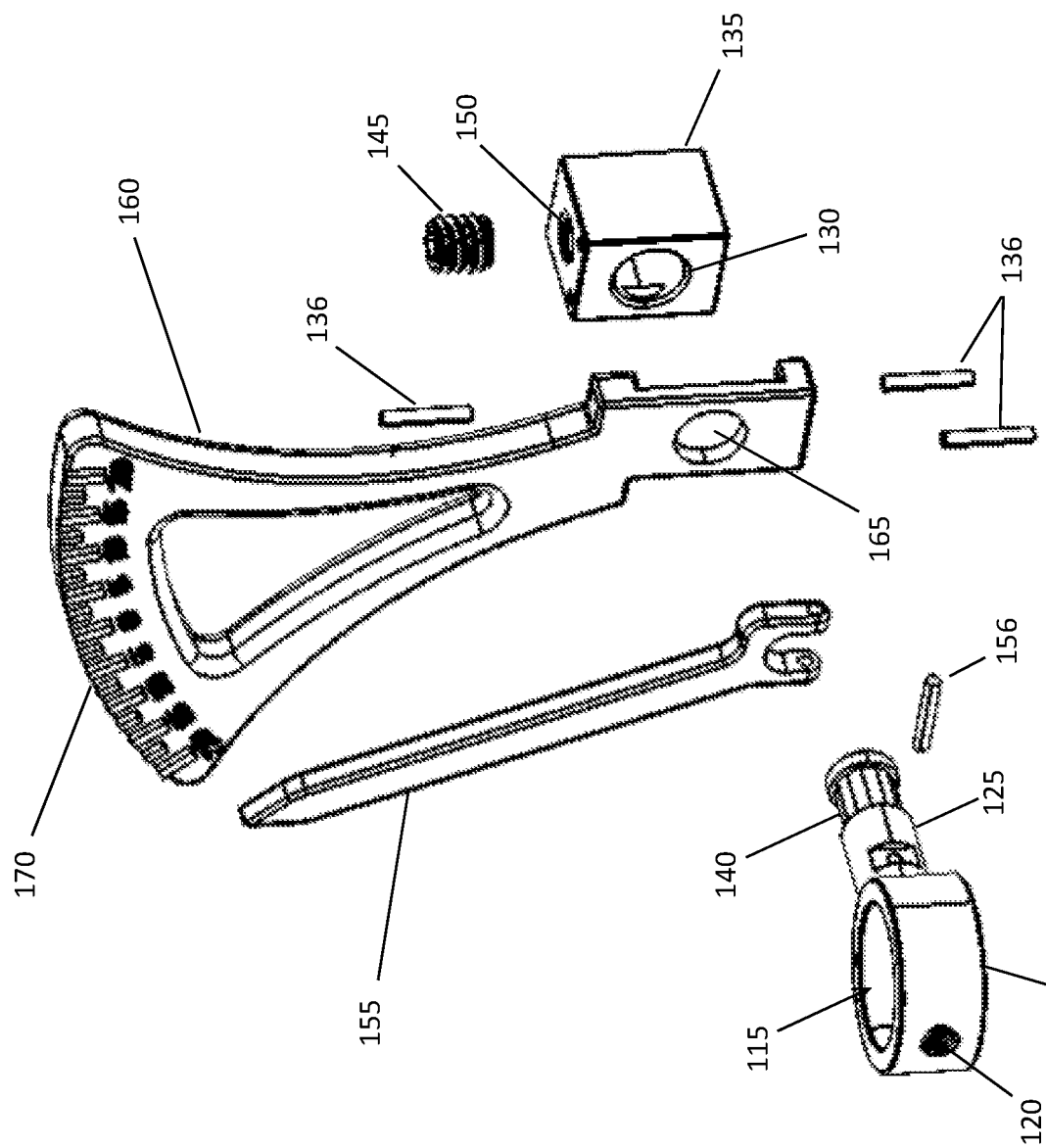
FIG. 3D is an exploded view of the indicating and readout arm and related frame structure of FIG. 3A.
Figure 4A:
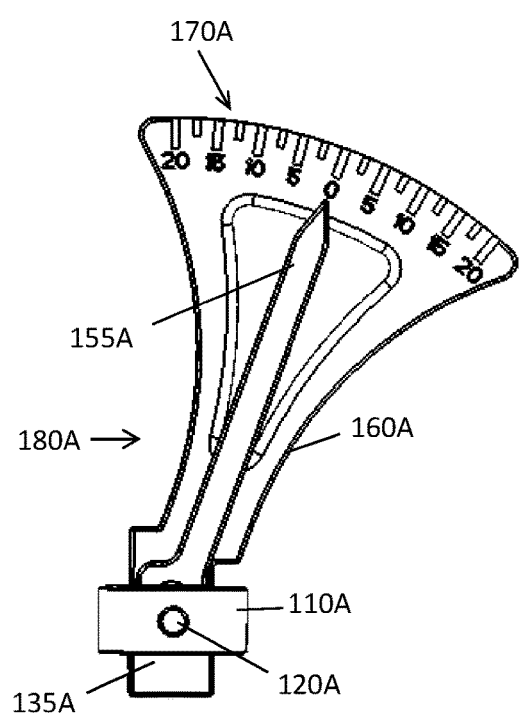
FIGS. 4A through 4D depict various perspective views of a right-side indicating and readout arm of the spinal alignment frame of FIG. 1.
Figure 4B:
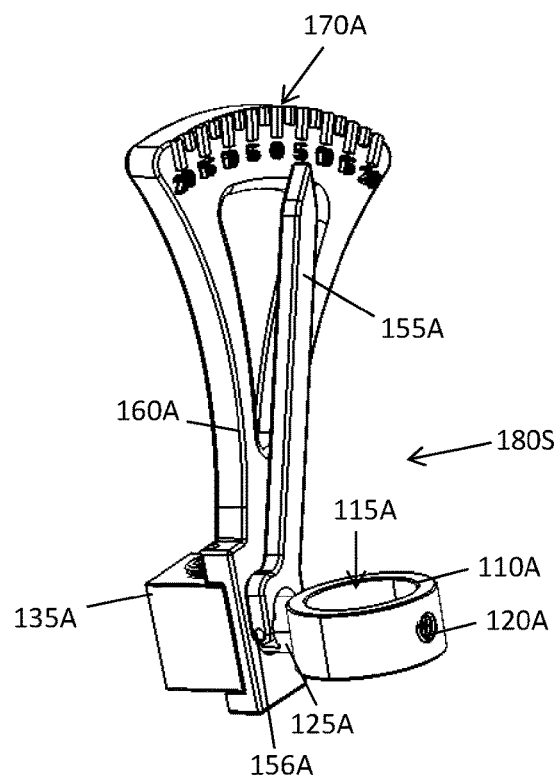
Figure 4C:
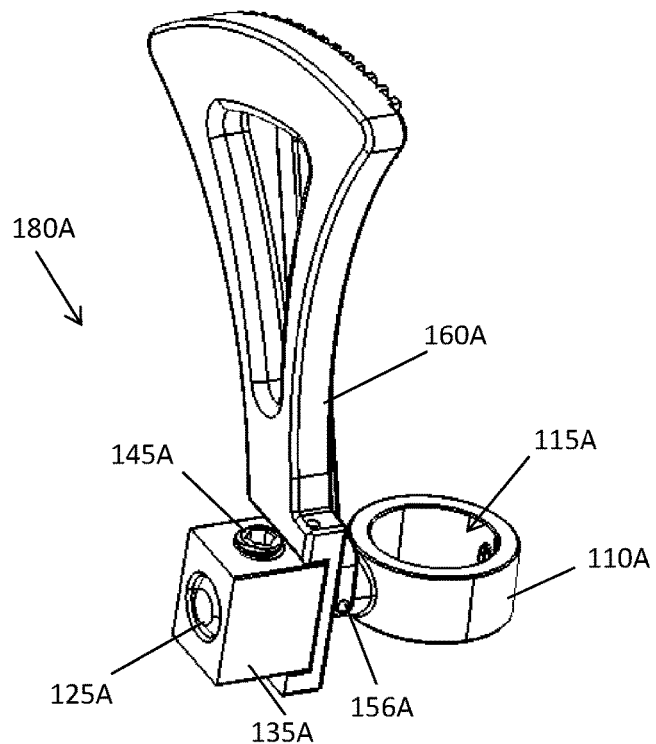
Figure 4D:
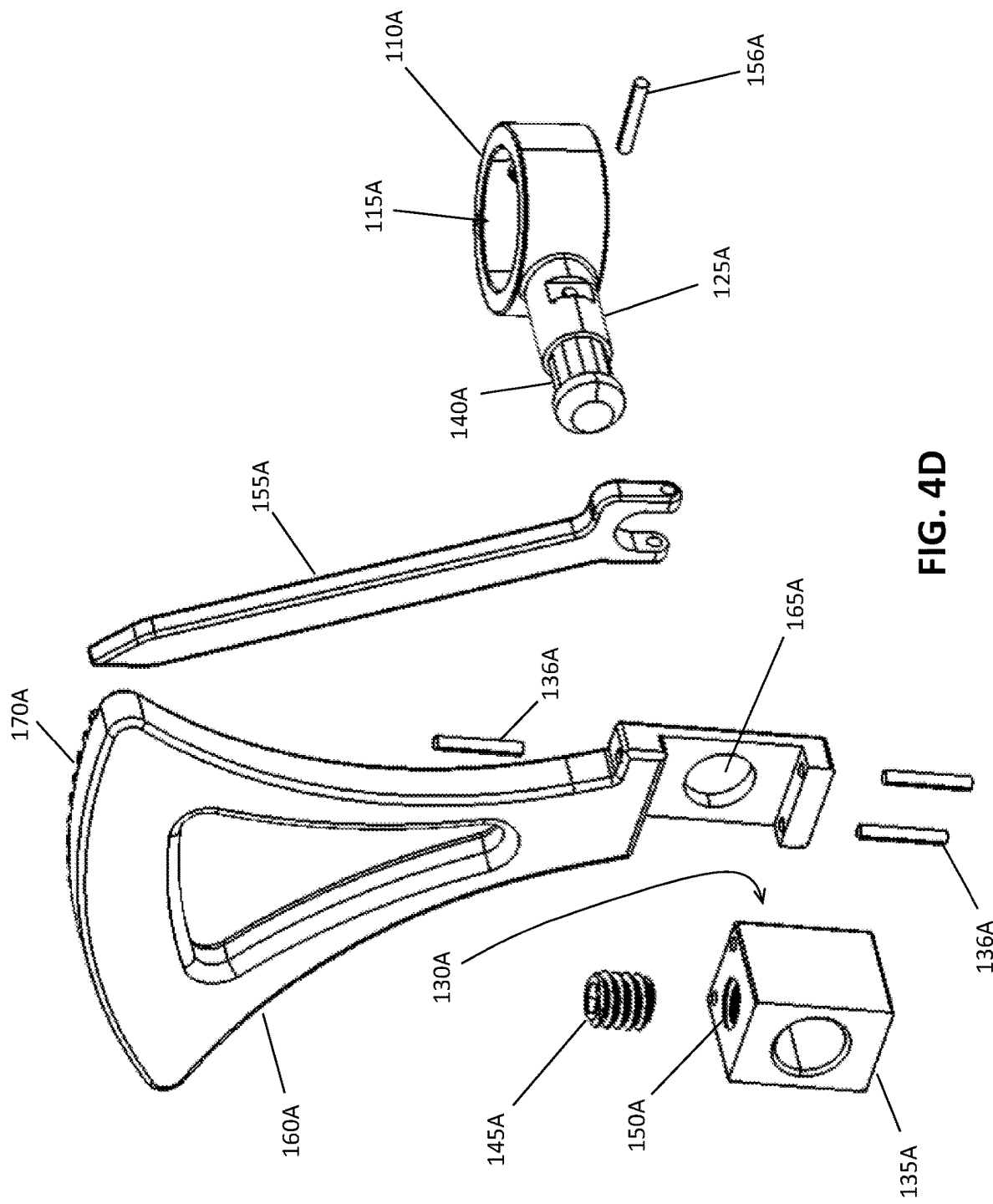

FIGS. 3A through 3D and 4A through 4D depict various perspective and exploded views of the indicating and readout arms and related frame structures. As best seen in FIGS. 3D and 4D, each ring 110 and 110A includes an attached ring shaft 125 and 125A. The ring shafts 125 and 125A are sized and configured to fit into corresponding openings 130 and 130A in first and second attachment blocks 135 and 135A attached to the frame (not shown). Each ring shaft 125 and 125A includes a grooved or reduced diameter section 140 and 140A that accommodates set screws 145 and 145A that secure through openings 150 and 150A in the attachment blocks 135 and 135A. The set screws 145 and 145A allow the ring shafts 125 and 125A to be inserted into the openings 130 and 130A and then the set screws 145 and 145A can be tightened a sufficient degree to retain the ring shafts 125 and 125A within the openings 130 and 130A in the first and second attachment blocks 135 and 135A, yet allow the ring shafts 125 and 125A to rotate freely about the longitudinal axes of the ring shafts 125 and 125A.

Each ring shaft 125 and 125A includes an indicator arm 155 and 155A which is secured to the ring shaft 125 and 125A by a pin 156 and 156A or other feature extending through the ring shaft 125 and 125A. The pin 156 and 156A desirably locks the indicator arm to the ring shaft such that rotation of the ring 110 and ring shaft 125 concurrently displaces and rotates the indicator arm 155 and 155A.

Readout arms 160 and 160A are secured to each of the first and second attachment blocks 135 and 135A by pins 136 and 136A, adhesives or other attachment features known in the art. Each readout arm 160 and 160A includes an opening 165 and 165A through which the respective ring shaft 125 and 125A can extend. An indicator scale 170 and 170A is included on each readout arm 160 and 160A. Because the readout arms 160 and 160A are secured to the blocks 135 and 135A, the readout arms 160 and 160A do not rotate with the ring shafts 125 and 125A, but rather are secured relative to the frame (not shown) to which the blocks 135 and 135A are attached. Because the readout arms 160 and 160A remain stationary relative to the frame, and the indicator arms 155 and 155A move with the ring shafts 125 and 125A, rotation of the rings 110 and 110A relative to the frame will rotate the indicator arms 155 and 155A relative to the readout arms 160 and 160A, and the relative rotational position between each indicator arm 155 and a corresponding readout arm 160 can be determined from each indicator scale 170 and 170A.

Figure 5:
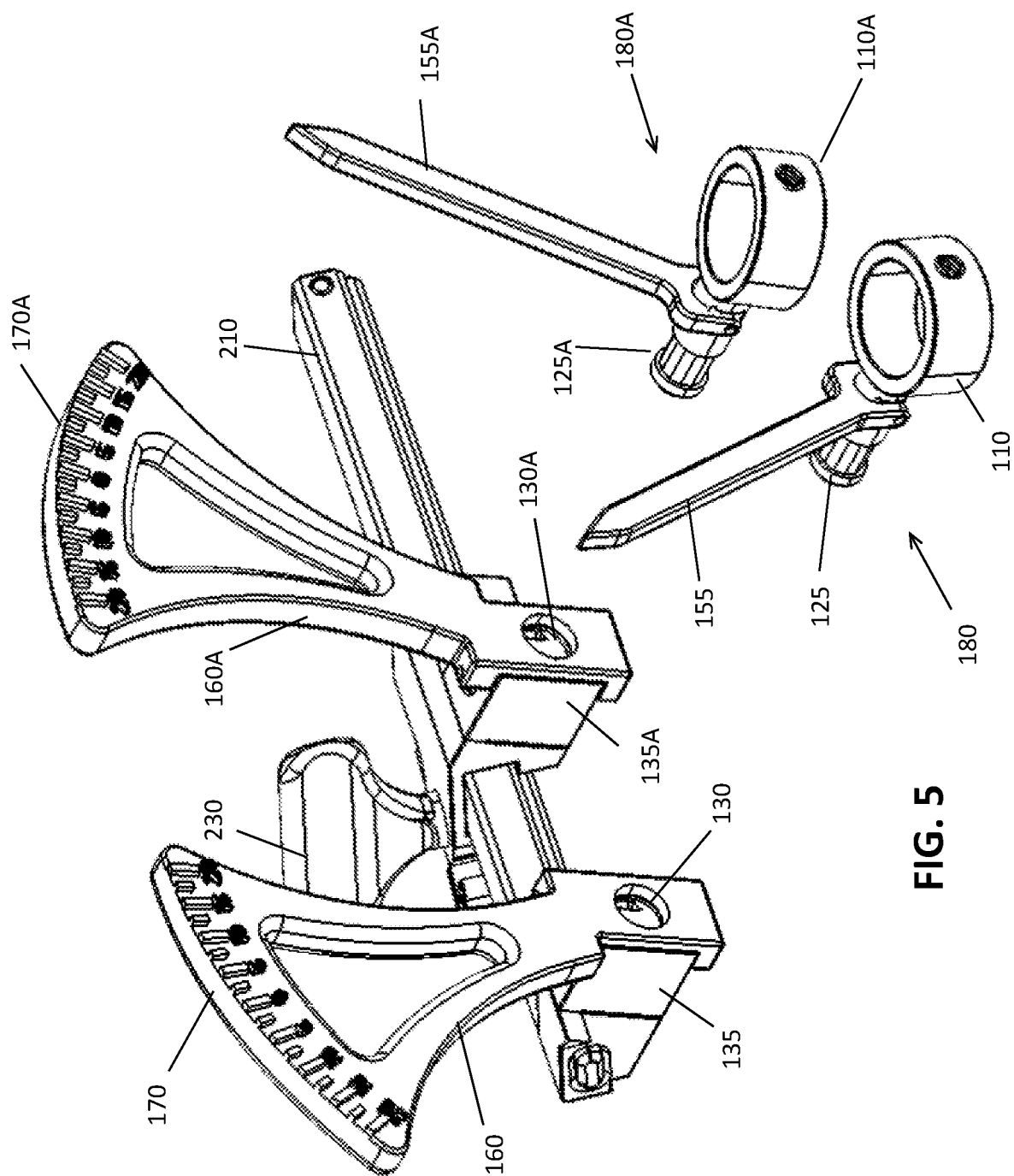
FIG. 5 is a perspective view of the spinal alignment frame of FIG. 2, with left and right indicator arm assemblies detached from the frame.

FIG. 5 depicts the measuring and distraction frame 100 assembly, showing left and right indicator arm assemblies 180 and 180A (i.e. rings, ring shafts, indicator arms, and associated coupling features) prior to insertion of the ring shafts 125 and 125A into the openings 130 and 130A in the first and second attachment blocks 135 and 135A. It should be understand that "left" and "right" are used for convenience only, and that various other embodiments could include reversed or other positioning arrangements for the various components described herein. In addition, the substitution of "left" and "right" with "first" and "second" or "cephalad" and "caudad," or other such conventions, could be used as desired, and are contemplated herein.

In one exemplary embodiment, the ring 110 of the left indicator arm assembly 180 can be slid over or otherwise engaged to a guide 20 and the ring shaft 125 inserted into the opening 130 in the first attachment block 135. The set screw (not shown) could then be tightened a sufficient amount to secure the ring shaft 125 to the first attachment block 135, yet allow the ring shaft 125 to rotate relative to the block 135, as previously discussed. Similar actions could be taken with the right indicator arm assembly 180A for another guide 20, which can be connected to the second attachment block 135A in a similar manner.

Figure 6:
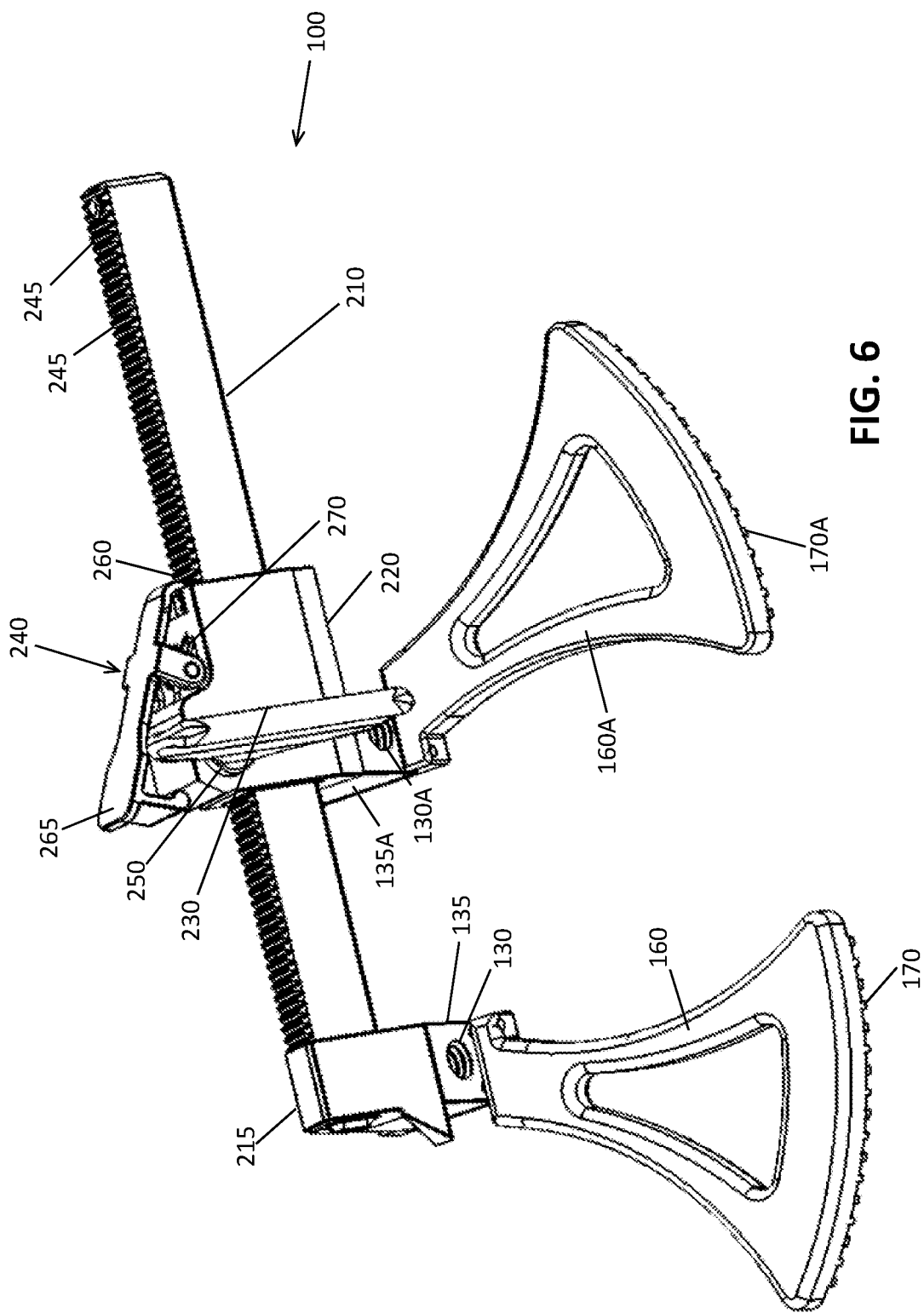
FIG. 6 is a perspective view of the backside of the spinal alignment frame of FIG. 5 the frame.

FIG. 6 depicts an upper perspective view of the alignment and distraction frame 100, showing an elongated rack 210, a left housing 215 and a right housing 220. The left housing 215 connects the first attachment block 135 to the elongated rack 210. The right housing 220 connects the second attachment block 135A to the elongated rack 210, with the right housing 220 capable of translation along the elongated rack, such that the spacing between the left housing 215 and the right housing 220 can be varied. The right housing 220 also includes a rotating adjustment thumb screw 230 that rotates a pinion engaged with rack 210 and a selective locking mechanism 240.

The elongated rack 210 includes a linear gear bar or toothed portion 245 along one side which extends through the right housing. Inside the right housing 220, a pinion or circular gear 250 engages with the toothed portion 245, with the circular gear 250 attached to the enlarged drive plate of the thumb screw 230. The selective locking mechanism of the right housing includes a locking tooth 260 at one end which engages with the toothed portion 245 of the elongated rack 210 to prevent translation of the right housing in an undesirable manner when the lock is engaged. The other end of the locking mechanism includes a push plate 265 which can be depressed to overcome the force of a biasing spring 270 that maintains the locking tooth 260 in contact with the toothed portion 240 of the elongate rack 210.

In this embodiment, to slide the right housing along the elongated rack 240, a user can depress the push plate 265, which disengages the locking tooth 260 from the toothed portion 245. The thumb screw 230 can then be rotated in a clockwise or counterclockwise direction, which rotates the circular gear 250 against the toothed portion 240 of the elongated rack 210 and drives the right housing 220 away from or towards the left housing. Once movement of the right housing 220 is no longer desired, the push plate 265 can be released, and the locking tooth 260 will re-engage with the toothed portion 245 of the rack 210. The locking plate itself may include a secondary lock (not shown) that holds the push plate in the disengaged position to relieve the user of the need to maintain continuous pressure on the push plate while also operating the thumb screw 230.

In alternative embodiments, the locking mechanism could include a variety of locking and/or unlocking modes, including a "free wheeling" or unlocked mode (i.e., an unlocked mode which allows the right housing to freely slide), a "closing detent" mode (i.e., a detent mechanism that allows sliding of the right housing towards the left housing, but inhibits motion in the other direction), an "opening detent" mode (i.e., a detent mechanism that allows sliding of the right housing away from the left housing, but inhibits motion in the other direction), a powered mechanism, linear sliders, and/or any other mechanism desired or known. The unlocked mode could be particularly useful during initial placement of the frame onto the tubular guides, as well as during the various distraction and/or correction operations, as it may be desirous to adjust the spacing between the housings to accommodate the initial placement of the left and right indicator arm assemblies and/or to facilitate the surgeon's manual movement of the guides 20 during rotation, distraction/compression and/or other corrective maneuvers.

Figure 7:
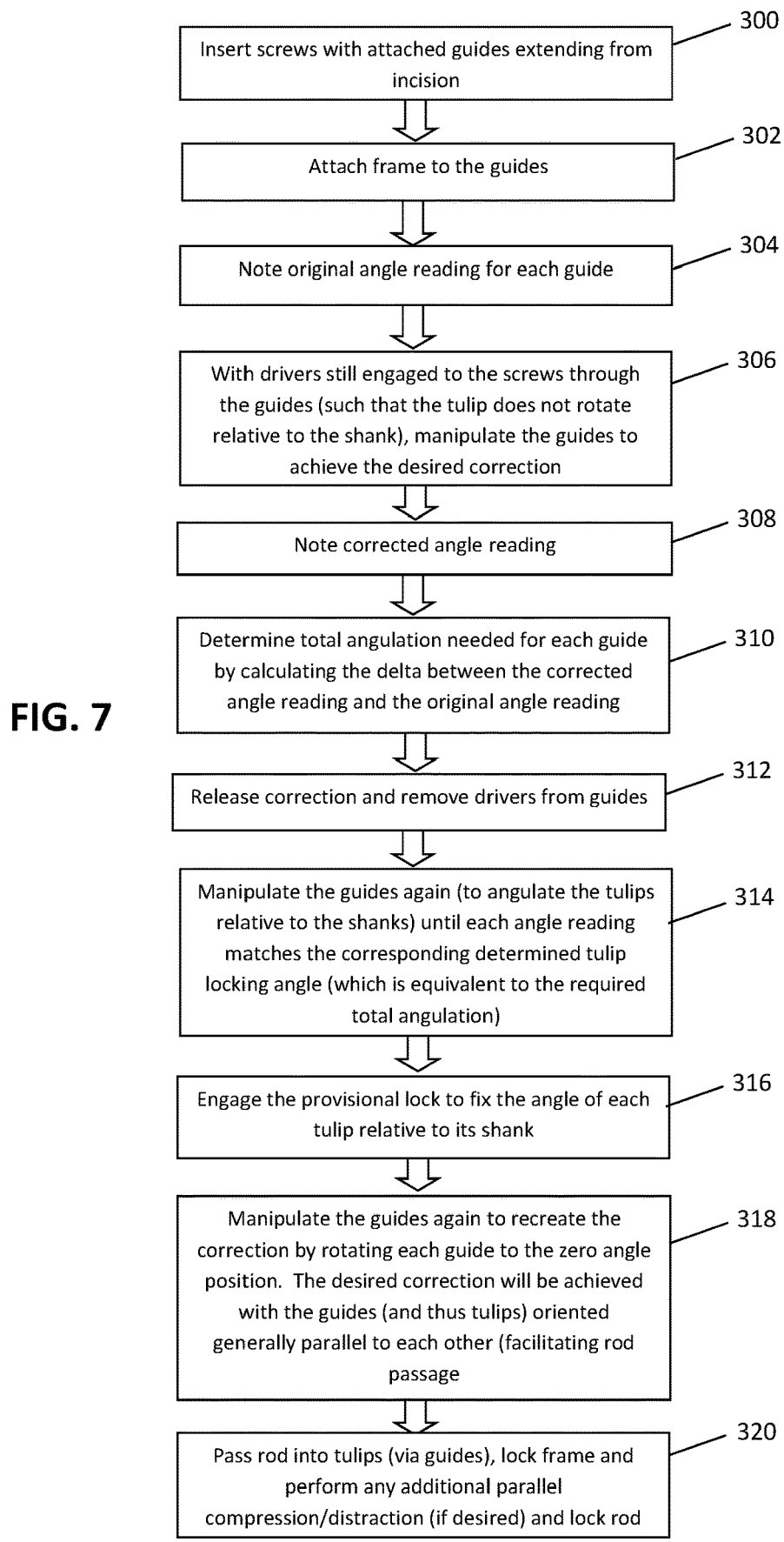
FIG. 7 is a flowchart denoting example steps of a method for performing a surgical procedure with the posterior fixation system and alignment frame of FIG. 1 to perform a surgical correction.

With reference to FIG. 7, one example method utilizing the spinal alignment and distraction frame 100 to correct a sagittal misalignment and fixate the correction is described. Initially, in step 300 first and second pedicle screws 12 are anchored into a superior vertebral body and an inferior vertebral body that are each adjacent to a fractured, compressed, misaligned, or resected vertebral body located there between. The vertebral body may be fractured, compressed, misaligned, or resected due a wide variety of pathologies, including osteoporosis, trauma, metastatic disease or other causes. The pedicle screws 12 are anchored with their respective guides 20 engaged to the housing 14 and extending out of the incision(s) used for installation. Drivers used to drive the screw shanks are left engaged to the shank and extending out of the guide lumen 28. Next the spinal alignment and distraction frame 100 is coupled to the installation guides 20 by sliding the ring connectors 110 and 110A over a respective guide (Step 302). Alternatively, the connection rings 110 and 110A can be attached to the guides 20 first, and thereafter the ring shafts 125 and 125A can be coupled to the frame. The frame permits one or more of the ring connectors to slide relative to the frame, allowing the spacing between the rings to be widened and/or narrowed as needed, and facilitating the sliding of the ring connections over the guides 20 (and drivers) and engaging set screws through the apertures 120 and 120A. For step 304, with the ring connectors 110 and 110A unlocked (that is, able to rotate relative to the frame), an initial angle reading is taken for each guide/ring connector combination. For example purposes, initial readings will be denoted as $A^I$ and $B^I$, with $A^I$ representing an angle value between the axis of the ring connector 110 (and attached guide 20) and the rack, and $B^I$ representing an angle value between the axis of the ring connector 110A (and attached guide 20) and the rack. Initial angle readings are noted for future reference. With the drivers sill engaged to the screw shanks (to in essence effect a provisional locking of the housing 14 relative to the shank), the guides 20 are manipulated to achieve the desired realignment or correction of the vertebrae (step 306) (which can be monitored or verified using fluoroscopy or other visualization techniques). When the desired correction is achieved, corrected angle readings are taken, denoted as $A^C$ and $B^C$ (for example purposes), from the readout indicators 170 and 170A (step 308). The readings $A^C$ and $B^C$ represent the angle of the respective guides 20, and thus the housings 14 also, relative to the rack 210. In step 310 the total angulation values needed to achieve the desired correction is determined, denoted herein (for example purposes) as $A^T$ and $B^T$. $A^T$ and $B^T$ are determined by calculating the delta between the corrected angle readings ($A^C$ and $B^C$) and the initial angle readings ($A^I$ and $B^I$), respectively. This can be accomplished by subtracting $A^C$ from $A^I$ and $B^C$ from $B^I$. Thus for example purposes only, if $A^I$ equals negative 3 and $A^C$ equals negative 8, then $A^T$ equals positive 5. Likewise, if $B^I$ equals positive 2 and $B^C$ equals negative 4, the $B^T$ equals positive 6. (In step 312, the correction may be released, and the drivers removed from the guides 20 (effectively unlocking the housing 14 relative to the shank). With the housings 14 free to move relative to the shanks, in step 314 the guides 20 are again manipulated, this time to align the guides 20 with the angle readings $A^T$ and $B^T$. While maintaining the angles $A^T$ and $B^T$, the provisional locking feature of the screws 12 is engaged (step 316), locking the housings relative to the shanks in the positions $A^T$ and $B^T$. This may be accomplished, for example, by advancing a provisional locking tool through the lumen 28 of each guide and engaging the locking mechanism.

Moving to step 318, the guides 20 are manipulated again, this time to maneuver the guides to the zero angle position. This adjustment to zero will provide the desired correction while simultaneously aligning the housings 14 generally parallel to each other such that the rod 18 can be passed (step 320) without custom bending and locked in place with locking caps.

Prior to locking the rod completely, the surgeon may also choose to lock the ring connectors 110 and 110A such that the rack may be utilized to apply parallel compression or distraction to the vertebrae by operating the thumb screw 230 to translate the housing 220 along the rack 210 in the appropriate direction. Once the final desired corrections and/or spinal alignment have been obtained (which may include desired lordotic or other curvature corrections, at the surgeon's options) the rod is finally locked. The frame 100 and guides 20 are disengaged and removed.

The disclosed system desirably provides for the accurate alignment and locking of polyaxial screw heads in desired rotational positions relative to their respective screw shanks already implanted into vertebral bodies in such a manner that later distraction and/or reduction of the vertebral bodies to a desired orientation can be accomplished using distraction, torque and rotational forces on the vertebral bodies through the attached pedicle screw shanks, with the resulting alignment of the pedicle screw heads being optimized for securement to a longitudinal spinal rod or other instrumentation without requiring bending of the rod or the use of specialized adapters. The described frame also facilitates the distraction and/or compression of the relevant spinal segment in a controlled fashion after a surgical correction and/or appropriate lordosis/curvature of the spine has been obtained but before final fixation of the spinal anatomy using instrumentation has been accomplished.

While specific embodiments have been shown by way of example in the drawings and described herein in detail, it will be appreciated that the invention is susceptible to various modifications and alternative forms (beyond combining features disclosed herein). The description herein of specific embodiments is not intended to limit the invention to the particular forms disclosed, but on the contrary, the invention is to cover all modifications, equivalents, and alternatives falling within the spirit and scope of the invention.

What is claimed is:

1. A spinal alignment frame for facilitating alignment of vertebrae in the spine of a patient in conjunction with the installation of a spinal fixation construct, the spinal fixation construct including a pair of pedicle screws each including an anchor and a polyaxial housing that rotates relative to the anchor and a connecting rod that couples between the housings, each of the housings also being releasable coupleable to a screw extension instrument that is configured to extend out of the patient from the housing, the spinal alignment frame comprising:

an elongated rack, a first coupler coupled to the elongated rack, the first coupler comprising a coupling ring configured to be releasably coupled to a screw extension instrument, the coupling ring connected to a shaft extending in a lateral direction perpendicular to a longitudinal direction of the screw extension instrument and a second coupler coupled to the elongated rack and configured to be releasably coupled to a guide, the guide with a distal end that couples to one of the housings, wherein the first coupler is rotatable relative to the elongated rack and includes an indicator that indicates an angle of the first coupler relative to the elongated rack, and wherein the second coupler is rotatable relative to the elongated rack and includes an indicator that indicates an angle of the second coupler relative to the elongated rack, at least one of the first coupler and the second coupler being translatable along the elongated rack.

2. The spinal alignment frame of claim 1, wherein the coupling ring and the shaft are rotatable about the lateral direction perpendicular to the longitudinal direction of the extension.

3. The spinal alignment frame of claim 1, wherein the indicator is configured to rotate with the coupling ring and the shaft, the rotation of the indicator arm relative to a readout arm is configured to be determined by an indicator scale, the indicator scale distributed in a plane perpendicular to the lateral direction perpendicular to the longitudinal direction of the screw extension instrument.

4. The spinal alignment frame of claim 3, wherein the readout arm is securely fixedly to a first attachment block, the first attachment block laterally offsets from the coupling ring and the indicator.

5. The spinal alignment frame of claim 3, wherein the readout arm comprises an opening through which the shaft is configured to extend.

6. The spinal alignment frame of claim 5, wherein the opening is connected with a groove extending laterally that fixedly couples to the first attachment block, the groove comprising a height along the longitudinal direction of the screw extension instrument sufficient to enclose a height of the first attachment block therewithin.

7. The spinal alignment frame of claim 1, wherein the indicator arm is perpendicular to the longitudinal direction of the screw extension instrument.

8. The spinal alignment frame of claim 1, wherein the shaft includes a reduced diameter section.

9. The spinal alignment frame of claim 8, wherein the reduced diameter section is sized and configured to fit at least partly into an opening in a first attachment block, the first attachment block laterally offsets from the coupling ring and the indicator.

10. The spinal alignment frame of claim 1, wherein the indicator arm is perpendicular to the longitudinal direction of the screw extension instrument.

11. The spinal alignment frame of claim 1, wherein the shaft includes a reduced diameter section.

12. The spinal alignment frame of claim 11, wherein the reduced diameter section is sized and configured to fit at least partly into an opening in a first attachment block, the first attachment block laterally offsets from the coupling ring and the indicator.

13. The spinal alignment frame of claim 1, wherein the shaft is sized and configured to fit into an opening in a first attachment block, the first attachment block laterally offsets from the coupling ring and the indicator.

14. A method of realigning spinal vertebrae and installing a spinal fixation construct, comprising the steps of:
  inserting a first shank of a first pedicle screw having an first adjustable housing into a first pedicle within a first vertebra;
  inserting a second shank of a second pedicle screw having an second adjustable housing into a pedicle second vertebra;
  connecting a first extension member to the housing of the first pedicle screw;
connecting a second extension member to the second housing of the second pedicle screw;
  connecting the first extension member to a first location on a rack member using a first rotatable coupler, the first rotatable coupler including a first coupling ring, a shaft, and a first indicating mechanism for indicating a relative alignment of the first extension member relative to the rack member, the first coupling ring, the shaft, and the first indicating mechanism rotatable laterally offset from the rack member,
  connecting the second extension member to a second location on the frame member using a second rotatable coupler, the second rotatable coupler including a second indicating mechanism for indicating a relative alignment of the second extension member relative to the frame member,
  obtaining a first measurement from the first indicating mechanism and a second measurement from the second indicating mechanism;
  while preventing relative motion between the first shank and the first housing and between the second shank and the second housing, manipulating the first and second extension members to move the first and second vertebra to a first desired relative alignment and obtaining a third measurement from the first indicating mechanism and a fourth measurement from the second indicating mechanism;
  aligning the first and second extension members to a second relative alignment based on the first, second, third, and fourth measurements;
  locking the relative motion between the first shank and the first housing and between the second shank and the housing;
  manipulating the first and second members to move the first and second vertebra to the first desired relative alignment; and
  attaching a fixation rod between the first and second pedicle screws.

15. A spinal alignment frame for facilitating alignment of vertebrae of a patient in conjunction with installation of a spinal fixation construct, the spinal fixation construct including a pair of pedicle screws each including an anchor and a housing and a connecting rod that couples between the housings, the spinal alignment frame comprising:
  an elongated rack;
  a first coupler coupled to the elongated rack, the first coupler comprising a coupling ring configured to be releasably coupled to a screw extension instrument, the coupling ring connected to a shaft extending in a lateral direction, wherein the first coupler is rotatable relative to the elongated rack and includes an indicator arm that indicates an angle of the first coupler relative to the elongated rack; and
  a second coupler coupled to the elongated rack and configured to be releasably coupled to a guide that couples to the connecting rod, wherein the second coupler is rotatable relative to the elongated rack and includes an indicator that indicates an angle of the second coupler relative to the elongated rack,
  wherein the coupling ring, the shaft, and the indicator arm are laterally offset from each other.

16. The spinal alignment frame of claim 15, wherein the coupling ring and the shaft are rotatable about the lateral direction perpendicular to the longitudinal direction of the extension.

17. The spinal alignment frame of claim 15, wherein the indicator is configured to rotate with the coupling ring and the shaft, the rotation of the indicator arm relative to a readout arm is configured to be determined by an indicator scale, the indicator scale distributed in a plane perpendicular to the lateral direction perpendicular to the longitudinal direction of the screw extension instrument.

18. The spinal alignment frame of claim 17, wherein the readout arm is securely fixedly to a first attachment block, the first attachment block laterally offsets from the coupling ring and the indicator.

19. The spinal alignment frame of claim 17, wherein the readout arm comprises an opening through which the shaft is configured to extend.

20. The spinal alignment frame of claim 19, wherein the opening is connected with a groove extending laterally that fixedly couples to the first attachment block, the groove comprising a height along the longitudinal direction of the screw extension instrument sufficient to enclose a height of the first attachment block therewithin.

* * * * *